(12) United States Patent
Baron et al.

(10) Patent No.: US 8,201,465 B2
(45) Date of Patent: Jun. 19, 2012

(54) METHOD FOR AUTOMATICALLY SAMPLING TRITIUM IN THE WATER VAPOR IN AIR

(75) Inventors: Yves Baron, Cherbourg Octeville (FR); Denis Maro, Cherbourg Octeville (FR)

(73) Assignees: Etat Francais (représenté par le Délégué general pour l'armement), Arcueil Cedex (FR); Institut de Radioprotection Et de Surete Nucleaire, Clamart (FR)

( * ) Notice: Subject to any disclaimer, the term of this patent is extended or adjusted under 35 U.S.C. 154(b) by 519 days.

(21) Appl. No.: 12/307,252

(22) PCT Filed: Jul. 3, 2007

(86) PCT No.: PCT/FR2007/001121
§ 371 (c)(1),
(2), (4) Date: Aug. 3, 2009

(87) PCT Pub. No.: WO2008/003853
PCT Pub. Date: Jan. 10, 2008

(65) Prior Publication Data
US 2009/0301228 A1 Dec. 10, 2009

(30) Foreign Application Priority Data
Jul. 4, 2006 (FR) ...................................... 06 06065

(51) Int. Cl.
*G01N 1/22* (2006.01)

(52) U.S. Cl. .................................................... 73/863.11
(58) Field of Classification Search ................. 73/863.11
See application file for complete search history.

(56) References Cited

U.S. PATENT DOCUMENTS
3,712,074 A   1/1973   Boissin ............................. 62/55
4,638,674 A   1/1987   Redmann ................... 73/863.12

FOREIGN PATENT DOCUMENTS
FR   2 528 321 A1   12/1983
JP   11-064532 A   3/1999
JP   11064532 A  *  3/1999
JP   2001-330695 A   11/2001
JP   2005-016980 A   1/2005

* cited by examiner

*Primary Examiner* — Hezron E Williams
*Assistant Examiner* — Tamiko Bellamy
(74) *Attorney, Agent, or Firm* — Blakely, Sokoloff, Taylor & Zafman

(57) ABSTRACT

The invention relates to the measurement of the tritium concentration of the water vapor in air and more particularly the subject of the invention is a method of automatically sampling tritium in the water vapor of air using a cold trap, of the type comprising a first step of condensing the water vapor of the air by cooling over a cold trap and a second step of recovering the ice formed in the previous step in the form of condensation liquid, characterized in that the air is contained in a sampling chamber (1) and is brought into contact with a cold trap (2, 4) which has been brought to a temperature below 0° C. and in that the liquid of the second step is obtained by warming the cold trap.

9 Claims, 1 Drawing Sheet

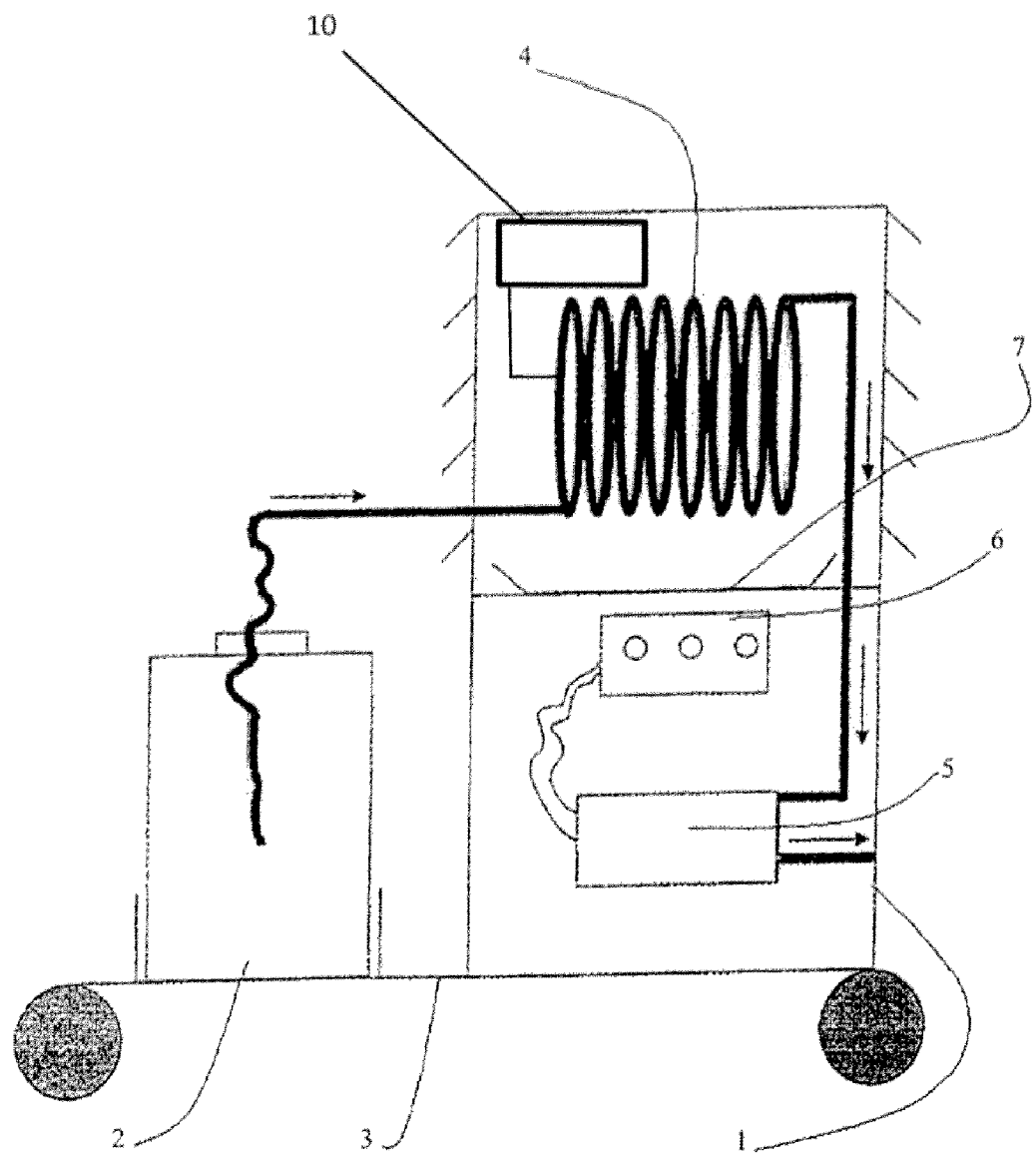

METHOD FOR AUTOMATICALLY SAMPLING TRITIUM IN THE WATER VAPOR IN AIR

The present patent application is a Utility claiming the benefit of Application No. PCT/PR2007/001121, filed Jul. 3, 2007.

The invention concerns the measurement of the tritium concentration in the water vapor in the air.

More specifically, the invention relates to a method for automatically sampling tritium in the water vapor in the air.

We know that sampling of tritiated water vapor can be done by trapping of the water vapor in the air using various means such as bubblers, desiccation agents or cold traps.

Sampling by bubbler consists of making air bubble in bottles containing water free from tritium, such as Abatilles water. The water vapor contained in the air is kept in the bottles. The water from the bottles is then sampled to measure its tritium concentration.

This system of sampling via bubbler has the drawback of requiring significant sampling time, in the vicinity of several days, due to a low sampling flow and to dilution of the tritium in the bottles of Abatilles water.

Another sampling method consists of causing air to pass in supports containing desiccation agents, such as molecular sieves or silica gals. The water vapor is retained in these supports provided with a large specific surface which grants them a strong adsorption power with regard to small polar molecules. In order to recover the water for the tritium assaying, it is necessary to perform an evaporation and condensation cycle of the water by heating of the support.

However, this method has drawbacks.

Due to their low water retention capacity, these systems can only be used in the environment with low rates of aspiration which lead to sampling periods in the vicinity of one week. Moreover, the recovery of the tritiated water for measurement requires a bulky installation and substantial and delicate manipulations. Lastly, these supports can only be used once in order to avoid any contamination of one sample by another.

In the cold trap sampling systems, the tritiated water vapor is trapped on a cold surface in order to cause its condensation. Static sampling devices exist in which the air is not agitated, as well as dynamic sampling devices where the air is agitated.

During static sampling, the cold trap is formed by a stainless steel plate placed directly in contact with the air and continuously cooled by dry ice or liquid nitrogen. The frost formed on the surface is recovered manually using a scraper. After warming of the frost, the tritium concentration is measured in the collected water using a known method.

The drawback of these devices is that they cannot be automated, due to the continuous cooling mode of the surfaces. Moreover, given that it is impossible to interrupt the cooling of the plate, there may be contamination of one sample by another.

In dynamic systems, contrary to static systems, the cold trap such as a Peltier effect or liquid nitrogen system, is not placed directly in the air, but arranged in a chamber. A pump causes the air to be analyzed to pass into this chamber where the vapor condenses continuously. In the case of the Peltier effect system, which can only be used with an air temperature above 0° C., the water is collected continuously and the tritium concentration can then be measured in the sample. In the system using liquid nitrogen, after stopping of the pump and warming of the cold trap by manual extraction, the tritium concentration is measured in the condensed water.

These dynamic sampling devices by cold trap also have drawbacks.

Due to the use of a pump, the quantity of water sampled is limited by the flow of the pump and imposes more substantial sampling times than with a static system. The system with the cold source realized by Peltier effect can only be used with an air temperature greater than 0° C., because it collects the water continuously and, moreover, isotopic fractionation of the sample may exist. The system with liquid nitrogen as cold source cannot be automated, as the sampling chamber continuously sinks into the liquid nitrogen tank. The recovery of the sample requires manual extraction from the chamber.

In order to resolve the drawbacks related to the known means explained above, we sought an automatic method, with great sensitivity, usable for air temperatures which can be lower than 0° C. and not creating contamination of one sample by another.

The object of the invention is a method for automatically sampling tritium in the water vapor in the air by cold trap, of the type comprising a first step of condensing the water vapor of the air by cooling over a cold trap and a second step of recovering the ice formed in the previous step in the form of condensation liquid, characterized in that the air is contained in a sampling chamber and is brought into contact with a cold trap which has been brought to a temperature below 0° C. and in that the condensation liquid is obtained by warming of the cold trap.

The warming is obtained by stopping the cooling produced by the cold trap.

The stopping of the cooling produced by the cold trap is completed by warming, when the outside temperature is below 0° C.

Preferably, the cold trap is formed by a coil connected to a tank of coolant.

The cold trap can also be coupled to a cryogenerator.

Advantageously, the cold trap is formed by a coil in which the liquid nitrogen pumped from a tank circulates.

Preferably, when warming of the cold trap is necessary, it is obtained through injection of hot air inside the coil, after disconnection from the liquid nitrogen tank.

The condensation liquid is collected by gravity in a receptacle arranged under the cold trap.

The invention also has for its object a device for the implementation of the method according to the invention, characterized in that it comprises an air sampling enclosure housing a cold trap with its operating means and a receptacle arranged under the cold trap and designed to collect the condensation liquid.

Preferably, this device comprises an air sampling enclosure housing a coil connected by a pump to an external liquid nitrogen tank and a receptacle arranged under the coil.

The method according to the invention has the following advantages

- great sensitivity, given that the sampling time is short because it is not limited by the flow of a pump and there is no dilution of the sample,
- automation, given that there is no manual intervention to recover the sample,
- possibility of use it temperatures below 0° C.,
- absence of contamination of one sample by another, given that the coil is dried by evaporation from one sample to the next,
- absence of isotopic fractionation of the sample.

The description will be better understood with the help of the non-limiting examples below illustrated by FIG. 1.

FIG. 1 is a diagrammatic view of an air sampling installation in the environment for the implementation of the method according to the invention.

EMBODIMENT

FIG. 1 comprises a "weather screen"-type sampling enclosure 1 made in stainless steel and a liquid nitrogen tank 2, all supported by a dolly 3.

The sampling enclosure 1 contains, in its upper part, a coil 4 formed by a copper tube composed of 14 non-contiguous spires and, in its low part, a pump 5 and a watertight electric board 6. Under the coil is arranged a receptacle 7 used to collect the condenser water under the coil.

The tank 2 and coil 4 form a cold trap to which is coupled a cryogenerator 10.

All of the installation, which has a length of 1.55 m for a width of 0.65 m and a height of 1.75 m and weighs 192 kg, is however easily movable thanks to its dolly.

In order to perform a sampling, one starts the pump 5 in order to evaporate the liquid nitrogen contained in the tank 2. While evaporating, the liquid nitrogen gradually cools the coil 4 and the water condensates on the spires of the coil.

One stops the pump 5 after 15 minutes. The ice formed on the spires reheats and is recovered by gravity in liquid form in the receptacle 7. If the temperature is too low to allow thawing of the ice, one can inject hot air inside the coil 4, after disconnecting it from the tank 2.

One recovers the water for analysis, in a known manner, by liquid scintillation, in order to measure the tritium concentration. The quantities collected vary depending on the meteorological conditions and are, on average, in the vicinity of 30 $cm^3$.

During a sampling, the atmospheric pressure, the temperature and the humidity of the air are measured by a PTU probe with a frequency of one Hertz. These meteorological measurements make it possible to convert the results of tritium measurements from the Bq.L-1 unit of sampled water into Bq.m-3 unit of air.

Comparison of the Method of the Invention and the Method by Bubbling:

The performance of the method according to the invention was evaluated in comparison with the bubbling method, which is the only method available on the market and the device for which is marketed under the name HAG 7000.

1. Evaluation of Sensitivity:

The method according to the invention makes it possible to perform samplings of a minimum volume of 10 $cm^3$ of water in 15 minutes, the average sampling being 30 $cm^3$. In order to obtain a volume of 10 $cm^3$ of water, which represents 0.67 $m^3$ of air, in the bubbling method, one must perform a sampling for 45 hours, the average flow of the bubbler being 15 L/h.

The method according to the invention therefore enables time savings by a factor of 180.

Furthermore, the dilution factor must be taken into account.

The bubbling method requires the use of several 180 $cm^3$ bottles of Abatilles water. Considering that the majority of the sampling is done in the first bottle, the dilution factor for a 45-hour sampling is then 18 relative a the method according to the invention, where one collects a volume of 10 $cm^3$.

Thus, considering the sampling time and the dilution factor, the method according to the invention makes it possible to decrease the detection limit for measurement of the tritium concentration by at least a factor of 3000.

2. Evaluation with Regard to Isotopic Discrimination:

Two experiments were conducted in order to assess the performance of the method of the invention relative to a possible problem with isotopic discrimination of the tritium relative to hydrogen, because isotopic discrimination can bias the representativeness of the measurements.

a) Result Obtained by the Method of the Invention with Tritiated Water Vapor of Known Concentration:

We generated, in a closed enclosure, water vapor with a known tritium concentration, then condensated this water vapor on the coil and collected it for measurement of the tritium by liquid scintillation. A comparison could then be made between the tritium concentration in the water vapor of known concentration and the tritium concentration of the water collected.

Water marked with tritium was placed in a receptacle under the coil of the installation illustrated in FIG. 1 in order to allow its evaporation naturally, then an aliquot was sampled for measurement.

A second receptacle was placed above the first, in order to recover, at the end of the experiment, the water whereof the tritium concentration is to be measured, which corresponds to the water vapor condensated on the coil. The assembly formed by the coil and the two receptacles was isolated from the outside through confinement of a volume of 35 L in vinyl.

Once placement was done, the pump of the installation was started, in order to perform the evaporation cycle of the water marked with tritium, then condensation on the coil. After 15 minutes, the pump was stopped and the condensates recovered in the second receptacle. The tritium concentration in the condensater water was measured by liquid scintillation.

During the experiment, the pressure, temperature and humidity of the air were measured, in order to take the quantity of water vapor initially present in the vinyl confinement into account. The experiment was repeated 5 times.

The average concentrations in the condenser water and the water marked with tritium are 252.8±15.1 $Bq.L^{-1}$ and 247.0±14.8 $Bq.L^{-1}$. There is therefore very good agreement between these two values. Furthermore, over the 5 experiments, the tritium concentrations in the condenser water varied little, since they were between 222.7±13.3 $Bq.L^{-1}$ and 262.0±15.7 $Bq.L^{-1}$, respectively. The tritium concentrations in the water marked with tritium ranged between 244.0±$Bq.L^{-1}$ and 257.0±$Bq.L^{-1}$. The average ratio between the tritium concentrations in the water marked with tritium and in the condenser water is 1.02.

Analysis of these results indicates that the method according to the invention allows the recovery of all of the tritium from the water vapor contained in the mass of air in which it is found.

The isotopic discrimination between the tritium and the hydrogen, although it exists physically, therefore does not influence the samplings done by the method of the invention.

b) Results Obtained Using the Method According to the Invention and the Method by Bubbling:

We compared the performance of the method of the invention with that of the method by bubbling with a bubbler of the HAG 7000 type commonly used in the nuclear industry. To this end, monitoring of the tritium concentration in the air during 4 periods of one week was done in a building containing used fuel storage ponds.

For a period of one week, a bubbler continuously sampled the water vapor with a flow of 20 $L.h^{-1}$. The vapor thus collected was analyzed by liquid scintillation.

During the same period, periodic samplings for 15 minutes and daily samplings were done, randomly, using the method according to the invention. Each sampling was analyzed by liquid scintillation.

Furthermore, the pressure, temperature and hygrometry of the air were measured during this period.

The values obtained during the 4 campaigns lasting one week each varied little during each week and from one week to the next.

The average values of the tritium concentration for weeks 1 to 4 are $0.50\pm0.03$ Bq.m$^3$, $0.46\pm0.03$ Bq.m$^3$, $0.38\pm0.02$ Bq.m$^3$ and $0.42\pm0.03$ Bq.m$^3$.

During the same weeks, the results obtained by bubbling are, for weeks 1 to 4, respectively: $0.49\pm0.03$ Bq.m$^3$, $0.54\pm0.03$ Bq.m$^3$, $0.41\pm0.02$ Bq.m$^3$ and $0.34\pm0.02$ Bq.m$^3$.

The average ratio between the results obtained by the method of the invention and the bubbler is 1.004.

There is therefore very good agreement between the results obtained by the method of the invention and those obtained with the HAG 7000 type bubbler.

The method according to the invention can be used to perform monitoring of the tritium concentration contained in the water vapor in the air in the environment, as well as in nuclear facilities, such as buildings housing cooling ponds.

The invention claimed is:

1. A method for sampling tritium in the water vapor in the air by cold trap, of the type comprising a first step of condensing the water vapor of the air by cooling over a part (4) of the cold trap (2, 4) and a second step of recovering the ice formed in the preceding step in the form of condensation liquid, wherein the air is contained in a sampling device (1) making it possible to eliminate the water from the sampled air, said sampling device being an enclosure (1) of the movable type for portability of the sampling device, said part (4) of the cold trap (2, 4) is located in the sampling device, a first step comprising actuating, for a determined duration, the cold trap (2, 4) which is brought to a temperature below 0 deg. C. through coolant circulating inside said part of the cold trap, so as to form ice on said part (4) of the cold trap, and a second step comprising warming said part (4) of the cold trap by stopping the cooling by the cold trap (2, 4) and making air circulating in said part during warming, and recovering the condensation liquid formed by the thawing of the ice.

2. The method according to claim 1, wherein the cold trap (2, 4) is formed by a coil (4) inside which circulates, on one hand, a coolant when the cold trap is actuated, and on the other hand, air during warming of the cold trap.

3. The method according to claim 2, wherein the coolant is pumped from a tank (2).

4. The method according to any one of claims 2 and 3, wherein during warming of the cold trap, the air circulating inside the coil is hot air.

5. The method according to claim 1, wherein the coolant (2) is liquid nitrogen.

6. The method according to claim 5, wherein the heating of the cold trap is obtained by injection of hot air inside the coil (4), after disconnection from the liquid nitrogen tank.

7. The method according to claim 1, wherein the condensation liquid is collected by gravity in a receptacle (7) arranged under the coil (4).

8. The method according to claim 1, wherein the cold trap is coupled to a cryogenerator.

9. A device for implementing the method according to claims 1 to 8, wherein the device comprises an air sampling enclosure (1) of the movable type housing a coil (4) connected by a pump (5) to an outside liquid nitrogen tank (2) and a receptacle (7) arranged under the coil (4).

* * * * *